(12) United States Patent
Jugl et al.

(10) Patent No.: US 12,059,556 B2
(45) Date of Patent: Aug. 13, 2024

(54) DATA COLLECTION APPARATUS FOR ATTACHMENT TO AN INJECTION DEVICE

(71) Applicant: Sanofi, Paris (FR)

(72) Inventors: Michael Jugl, Frankfurt am Main (DE); Michael Schabbach, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 17/946,476

(22) Filed: Sep. 16, 2022

(65) Prior Publication Data

US 2023/0073649 A1     Mar. 9, 2023

Related U.S. Application Data

(63) Continuation of application No. 16/957,229, filed as application No. PCT/EP2018/086104 on Dec. 20, 2018, now Pat. No. 11,524,119.

(30) Foreign Application Priority Data

Dec. 28, 2017   (EP) ..................................... 17306955

(51) Int. Cl.
*A61M 5/315*     (2006.01)
*A61M 5/24*     (2006.01)
(Continued)

(52) U.S. Cl.
CPC ............ *A61M 5/3155* (2013.01); *A61M 5/24* (2013.01); *G16H 20/17* (2018.01);
(Continued)

(58) Field of Classification Search
CPC .................. A61M 5/3155; A61M 5/24; A61M 2005/3126; A61M 2205/3306;
(Continued)

(56) References Cited

U.S. PATENT DOCUMENTS

2016/0235925 A1\*   8/2016   Kuhn ................ A61M 5/31525
2016/0287802 A1   10/2016   Blancke et al.
(Continued)

FOREIGN PATENT DOCUMENTS

CN     102413759     4/2012
CN     105377328     3/2016
(Continued)

OTHER PUBLICATIONS

International Preliminary Report on Patentability in International Appln. No. PCT/EP2018/086104, dated Jun. 30, 2020, 7 pages.
(Continued)

*Primary Examiner* — Abdul-Samad A Adediran
(74) *Attorney, Agent, or Firm* — Fish & Richardson P.C.

(57) ABSTRACT

A data collection device comprises an attachment assembly for attaching the data collection device to a dose setting dial of a medicament administration device and a sensor configured to detected an identifier provided on a surface of an internal component of the medicament administration device, the sensor comprising an ultrasound sensor configured to detect a geometric identifier formed on the surface of the internal component of the medicament administration device. A system comprises the data collection device and the medicament administration device.

19 Claims, 4 Drawing Sheets

(51) Int. Cl.
  *G16H 20/17* (2018.01)
  *A61M 5/31* (2006.01)

(52) U.S. Cl.
  CPC .............. *A61M 2005/3126* (2013.01); *A61M 2205/3306* (2013.01); *A61M 2205/3317* (2013.01); *A61M 2205/52* (2013.01); *A61M 2205/581* (2013.01); *A61M 2205/587* (2013.01)

(58) Field of Classification Search
  CPC ...... A61M 2205/3317; A61M 2205/52; A61M 2205/581; A61M 2205/587; A61M 5/31525; A61M 5/31528; G16H 20/17
  See application file for complete search history.

(56) References Cited

U.S. PATENT DOCUMENTS

| | | |
|---|---|---|
| 2016/0287808 A1 | 10/2016 | Madsen |
| 2017/0032211 A1 | 2/2017 | Allerdings et al. |
| 2018/0154086 A1* | 6/2018 | Toporek ............ A61M 5/31528 |

FOREIGN PATENT DOCUMENTS

| | | | | |
|---|---|---|---|---|
| DE | WO 2016/198516 | * | 12/2016 | ........ A61M 5/31551 |
| EP | 3042676 | | 7/2016 | |
| EP | 3058970 | | 8/2016 | |
| JP | H03-106418 | | 11/1991 | |
| JP | 2016-526424 | | 9/2016 | |
| WO | WO 2010/098929 | | 9/2010 | |
| WO | WO 2012/046199 | | 4/2012 | |
| WO | WO 2015/001008 | | 1/2015 | |
| WO | WO 2016/198516 | | 12/2016 | |
| WO | WO 2017/116957 | | 7/2017 | |

OTHER PUBLICATIONS

International Search Report and Written Opinion in International Appln. No. PCT/EP2018/086104, dated Mar. 25, 2019, 10 pages.

* cited by examiner

DATA COLLECTION APPARATUS FOR ATTACHMENT TO AN INJECTION DEVICE

CROSS REFERENCE TO RELATED APPLICATIONS

The present application is a continuation of U.S. patent application Ser. No. 16/957,229, filed Jun. 23, 2020, which is the national stage entry of International Patent Application No. PCT/EP2018/086104, filed on Dec. 20, 2018, and claims priority to Application No. EP 17306955.0, filed on Dec. 28, 2017, the disclosures of which are incorporated herein by reference.

TECHNICAL FIELD

The present disclosure relates to a data collection device for attachment to an injection device and collecting medicament dosage information therefrom.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing the dosage knob or an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin dose.

EP 3,058,970 relates to a data collection device for attachment to an injection device, including a sensor arrangement to detect moment of a moveable component of the injection device during delivery of a medicament.

WO 2012/046199 relates to a dosage monitoring device for use in conjunction with a liquid dispenser, including a dispensing sensor for sensing when a dosage is dispensed and a quantity sensor for determining the quantity of the dispensed dosage.

SUMMARY

In general, in one aspect, a data collection device comprises an attachment assembly for attaching the data collection device to a dose setting dial of a medicament administration device, and a sensor configured to detected an identifier provided on a surface of an internal component of the medicament administration device; the sensor comprising an ultrasound sensor configured to detect a geometric identifier formed on the surface of the internal component of the medicament administration device.

In some examples, the sensor is supported on a side of the data collection device which abuts the dose setting dial of the drug delivery device.

In some examples, the attachment assembly is configured to releasably attach the data collection device to the dose setting dial of the medicament administration device such that the dose setting dial of the medicament administration device is disposed between the sensor and the surface of the internal component.

In some examples, the data collection device comprises a processor arrangement configured to receive signals from the sensor and to determine identity of a medicament delivered from the medicament administration device, based on the detected identifier.

In some examples, the processor arrangement is further configured to detect the occurrence of a medicament delivery from the medicament administration device.

In some examples, the processor arrangement is configured to determine a time stamp for the detected occurrence of a medicament delivery and to store the determined medicament dosage and said time stamp.

In some examples, the identifier is provided on the surface of an internal component which rotates during a medicament delivery, and the processor arrangement is configured to determine, from the signals receives from the optical sensor, an amount of rotation of the internal component.

In general, in another aspect, a system comprises a medicament administration device comprising a dose setting dial and an internal component that rotates around a longitudinal axis of the device when a dose of medicament is delivered from the device the internal component includes an identifier formed on a surface thereof, and the data collection device is configured as described above.

In general, in another aspect, a system comprises a medicament administration device comprising a dose setting dial and an internal component that rotates around a longitudinal axis of the device when a dose of medicament is delivered from the device. The internal component includes an identifier formed on a surface thereof. The system also comprises a data collection device comprising an attachment assembly for attaching the data collection device to the dose setting dial, and a sensor configured to detected an identifier provided on a surface of an internal component of the medicament administration device, the sensor comprising an ultrasound sensor configured to detect a geometric identifier formed on the surface of the internal component of the medicament administration device.

In some examples, the sensor is supported on a side of the data collection device which abuts the dose setting dial of the drug delivery device.

In some examples, the attachment assembly is configured to releasably attach the data collection device to the dose setting dial of the medicament administration device such that the dose setting dial of the medicament administration device is disposed between the sensor and the surface of the internal component.

In some examples, the data collection device comprises a processor arrangement configured to receive signals from the sensor and to determine identity of a medicament delivered from the medicament administration device, based on the detected identifier.

In some examples, the processor arrangement is further configured to detect the occurrence of a medicament delivery from the medicament administration device.

In some examples, the processor arrangement is configured to determine a time stamp for the detected occurrence of a medicament delivery and to store the determined medicament dosage and said time stamp.

In some examples, the identifier is provided on the surface of an internal component which rotates during a medicament delivery, and the processor arrangement is configured to determine, from the signals receives from the optical sensor, an amount of rotation of the internal component.

These and other aspects of the disclosure will be apparent from and elucidated with reference to the embodiments described hereinafter

BRIEF DESCRIPTION OF THE FIGURES

Example embodiments will now be described with reference to the accompanying figures, of which.

DETAILED DESCRIPTION

In the following disclosure, embodiments will be described with reference to an insulin injection device. The present disclosure is however not limited to such application and may equally well be deployed with injection devices that eject other medicaments.

Figure 1:
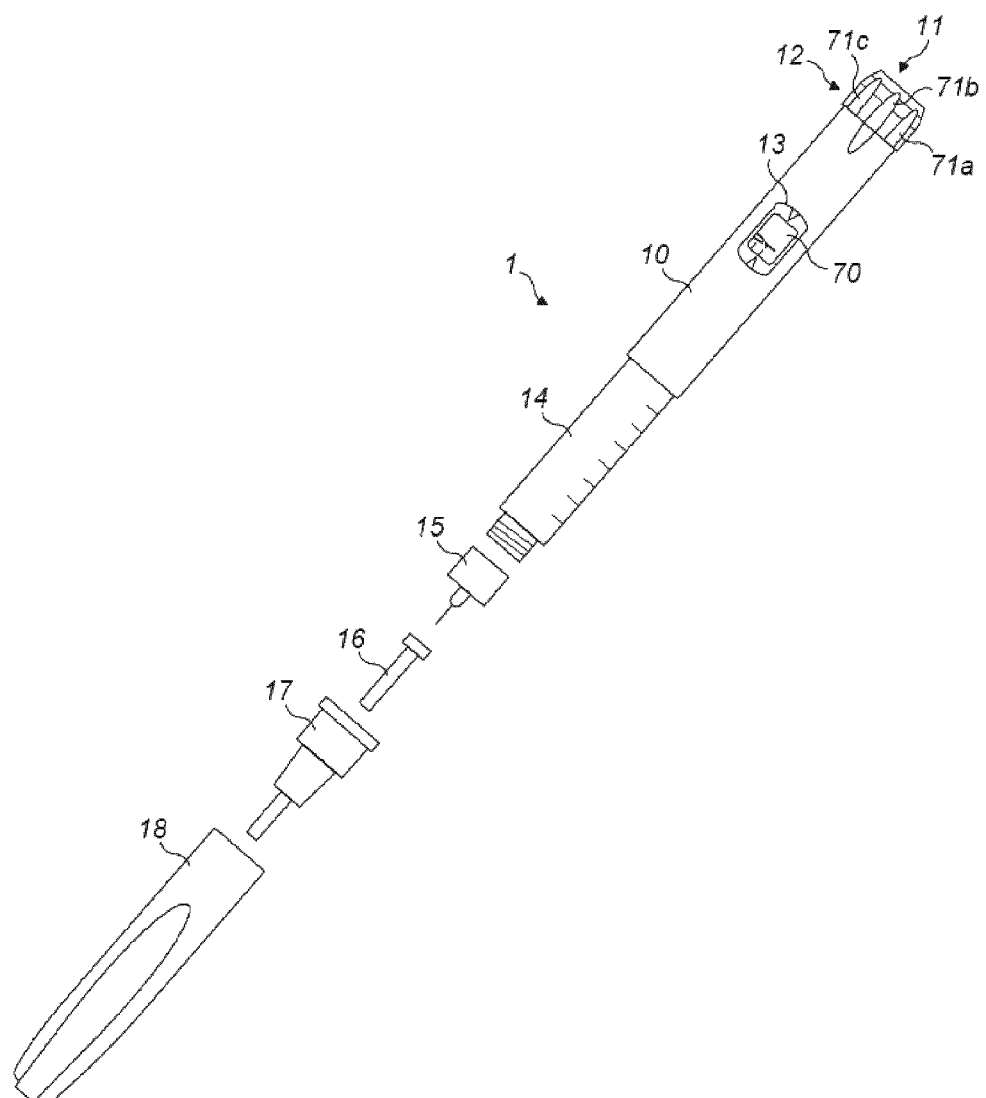
FIG. 1 shows an exploded view of an injection device for use with a data collection device.

FIG. 1 is an exploded view of a medicament administration device. In this example, the medicament administration device is an injection device 1, such as Sanofi's AllStar® insulin injection pen, however the present disclosure is also compatible with other types and makes of injection pens as described below.

The injection device 1 of FIG. 1 is a pre-filled injection pen that comprises a housing 10 and contains an insulin container 14, to which a needle 15 can be affixed. The injection device 1 may be disposable or re-usable. The needle is protected by an inner needle cap 16 and either an outer needle cap 17 or an alternative cap 18. An insulin dose to be ejected from injection device 1 can be programmed, or 'dialed in' by turning a dosage knob 12 (also referred to herein as a dose selection element 12), and a currently programmed dose is then displayed via dosage window 13, for instance in multiples of units. For example, where the injection device 1 is configured to administer human insulin, the dosage may be displayed in so-called International Units (IU), wherein one IU is the biological equivalent of about 45.5 micrograms of pure crystalline insulin (1/22 mg). Other units may be employed in injection devices for delivering analogue insulin or other medicaments. It should be noted that the selected dose may equally well be displayed differently than as shown in the dosage window 13 in FIG. 1.

The dosage window 13 may be in the form of an aperture in the housing 10, which permits a user to view a limited portion of a number sleeve 70 that is configured to move when the dosage knob 12 is turned, to provide a visual indication of a currently programmed dose. Alternatively, the number sleeve 70 may remain stationary during the dose dialling phase, and the dosage window 13 may move as a dose is dialed in to reveal the number corresponding to the dialed dose. In either case, the number sleeve 70 may be a component which rotates when a dose is being dispensed from the injection device 1.

In this example, the dosage knob 12 includes one or more formations 71a, 71b, 71c that facilitate programming because they improve the grip a user feels when grasping the dosage knob 12. In another example (not shown) the dosage knob does not include formations.

Attaching a data collection device does not require the dosage knob having formations. Having a tight fit and/or using rubber-like material at the contact surface between the data collection device and the injection device would provide an attachment that, on the one hand, facilitates a stable connection in the sense that the two devices remain attached to each other and, on the other hand, allows the two devices to be separated when intended to. The rubber-like material would ensure a proper fit even on a smooth surface, e. g, a dosage knob having a smooth surface such that that rotation of the data collection device causes rotation of the dosage knob and vice versa.

The injection device 1 may be configured so that turning the dosage knob 12 causes a mechanical click sound to provide acoustical feedback to a user. The number sleeve 70 mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose may also cause a mechanical click sound, which is however different from the sounds produced when using dosage knob 12. In some other embodiments, the injection device 1 does not have a separate injection button 11 and a user depressed the entire dosage knob 12, which moves longitudinally relative to the housing 10, in order to cause the medicament to be dispensed.

In the various embodiment, during delivery of the insulin dose, the dosage knob 12 is turned to its initial position in an axial movement, that is to say without rotation, while the number sleeve 70 is rotated to return to its initial position, e.g. to display a dose of zero units.

Injection device 1 may be used for several injection processes until either the insulin container 14 is empty or the expiration date of the medicament in the injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user. Nevertheless, differences (e.g. losses) between the ejected amounts and the injected doses may need to be taken into account.

Figure 2:
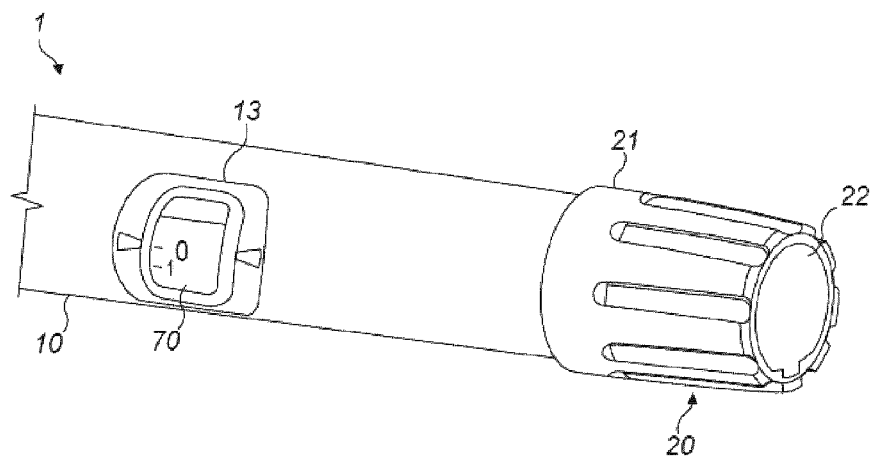
FIG. 2 depicts a data collection device, attached to the injection device of FIG. 1.

FIG. 2 is a perspective view of one end of the injection device 1 when a data collection device 20 according to an example embodiment is attached. The data collection device 20 includes a housing 21 with an end plate 22 forming a user interaction surface. The housing 21 may support an optical user feedback such as one or more LEDs (not shown). In some optional embodiments, the data collection device 20 comprises a display (not shown)

The data collection device 20 is compatible with a number of existing injection devices 1. The data collection device 20 is compatible with injection devices having a separate dose delivery button or an integrated dial. The data collection device 20 is compatible with injection devices where the dose setting dial does not rotate during dose administration, but where an internal component close to the dose setting dial does rotate during dose administration. The data collection device 20 allows the rotation of this internal component to be detected and measured.

Figure 3:
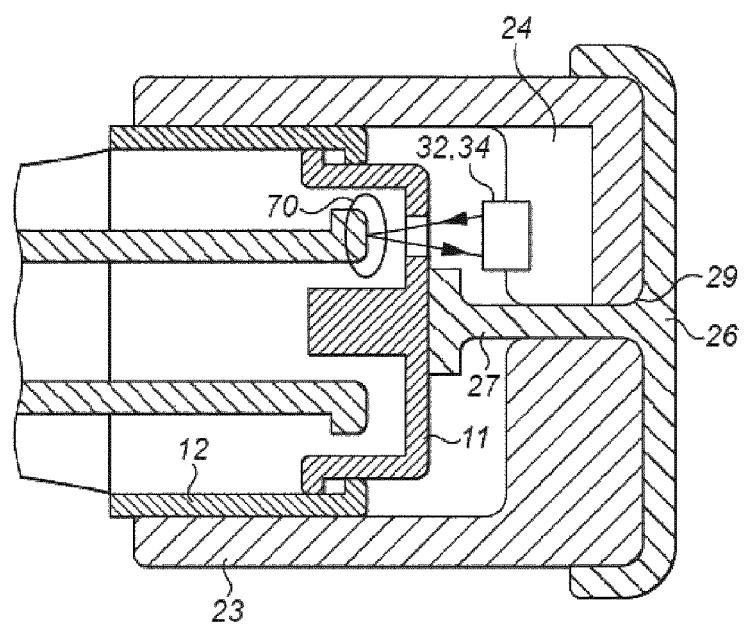
FIG. 3 is a cross-sectional view of a data collection device when attached to a first type of injection device.

FIG. 3 is a cross-sectional view of the data collection device 20 according to some embodiments, when attached to a first type of injection device 1.

In these embodiments, the injection device 1 is of a type having a dose setting dial 12 with a depressible dose delivery button 11, which a user would normally depress in order to activate the dispensing mechanism. The dose setting dial 12 is configured to be rotated to set a dose. In some injection devices, rotation of the dose setting dial 12 causes an internal spring to be tensioned, or the device may have a pre-tensioned spring. The dose setting dial 12 does not move longitudinally during dose setting. The dose setting dial 12 remains stationary during dose dispensing. For some other injection devices rotation of the dose setting dial 12 also causes the dose setting dial to move proximally out of the housing 10. When a dose is dispensed from the injection device 1, the dose setting dial moves back (distally) into the housing, but does not rotate. In either case, an internal component 70, such as a number sleeve 70, rotates during dose dispense. The data collection device 20 is configured so as to detect and measure the rotation of this internal component 70 when attached to the injection device 1.

The data collection device 20 includes a housing 21, an electronics assembly 24 disposed inside the housing 21 and a button 26 which protrudes from the proximal end of the housing 21 and is moveable longitudinally with respect to the housing 21. The housing 21 comprises an attachment assembly 23 configured to secure the data collection device 20 to the dose setting dial 12. The formations 71a, 71b, 71c on the dose setting dial 12 may be used to facilitate attachment of the data collection device 20.

In this particular example, the attachment assembly 23 is a sleeve that is positioned over the dose setting dial 12 through formations, not shown, that co-operate with the formations 71a, 71b, 71c on the dose setting dial 12 so that, when the dose setting dial 12 rotates during programming of the dosage, the data collection device 20 also rotates. Alternatively, or additionally, resilient padding, such as a foam rubber pad 44, may be provided within the formations on the attachment assembly 23, to allow for tolerances in the dimensions of the formations on the attachment assembly 23 and the formations 71a, 71b, 71c on the dose setting dial 12 and/or to provide an engagement between the attachment assembly 23 and the dose setting dial 12 so that rotation of the attachment assembly 23 causes rotation of the dose setting dial 12 and vice versa. Further alternatively, the attachment assembly 23 comprises a resilient padding of sufficient thickness to render formations that co-operate with the formations 71a, 71b, and 71c on the dose setting dial. The padding is soft enough to conform to the surface of the dose setting dial 12. For example, the padding is soft enough to conform to the formations on the surface of the dose setting dial 12.

The electronics assembly 24 is retained within the housing 21 such that it can move longitudinally with respect to the housing. The distal side of the electronics assembly 24 is configured to abut the dose delivery button 11 when the data collection device 20 is attached to the injection device. The proximal side of the electronics assembly 24 abuts or is integral with the button 26. The button 26 and electronics assembly 24 may form a single subassembly. The attachment assembly 23 may form another subassembly. In this embodiment, the two subassemblies are able to move longitudinally relative to each other, but cannot rotate relate to each other. The button 26 provides the finger rest for the user and the push surface for transmitting a push force to the dose delivery button 11 of the injection device. The result of this configuration is that when the button 26 of the data collection device 20 is depressed, the force is transferred through the electronics assembly 24 to the dose delivery button 11, causing it to be depressed.

The electronics assembly 24 comprises a PCB 28 and a battery 30, for example in the form of a coin cell. The PCB 28 may support a number of components including a processor arrangement 50, an ultrasonic source 32 and an ultrasonic detector 34. As shown in FIG. 3, in some embodiments, the ultrasonic source 32 and ultrasonic detector 34 are supported on the side of the PCB which abuts the dose delivery button 11. The dose delivery button 11 is transparent or substantially transparent to ultrasonic sound. Thus the sound emitted by the ultrasonic source 32 passes through the dose delivery button 11 and is reflected by the internal components. In particular the number sleeve 70 is a hollow cylinder which extends to the proximal end of the housing 10 and is releasably fixed to the dose setting dial 12. The annular end surface of the number sleeve 70 therefore sits underneath the dose delivery button 11 and is in the path of the emitted ultrasonic sound. The number sleeve 70 is provided with a three-dimensional geometric pattern on the annular end surface. For example, raised and non-raised sections may be arranged alternately. Alternatively, a pattern of holes may be spaced around the annular end surface.

During a dose dispensing operation, the ultrasonic source 32 emits ultrasonic sound against the part of the number sleeve 70 including the pattern of relatively raised and non-raised regions; and the ultrasonic detector 34 receives the sound reflected by the pattern. The output of the ultrasonic detector 34 is relayed to the processor 50 which determines the pattern on the annular end surface of the number sleeve 70.

Figure 4A:
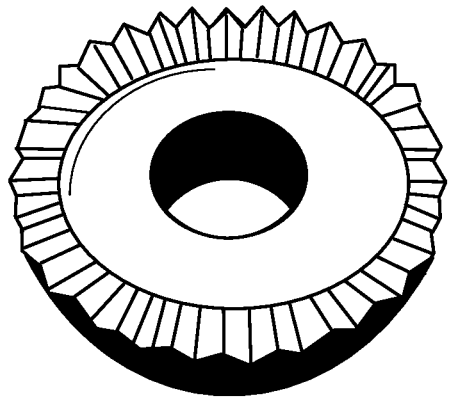
FIGS. 4A and 4B are internal views of an injection device for use with the first type of data collection device.

FIG. 4A shows a first example of a pattern formed on the annular end surface of the number sleeve 70. The end surface of the number sleeve 70 is provided with a pattern of relatively raised and non-raised regions. In an example, the raised regions are in the form or a plurality of teeth, arranged to extend from the end surface of the number sleeve in an axial direction of the device. The plurality of teeth may be formed with a particular shape or profile. The shape or profile of the teeth may identify the medicament.

Figure 4B:
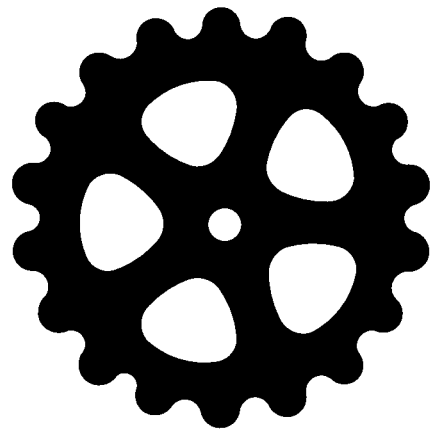

FIG. 4B shows a second example of a pattern formed on the annular end surface of the number sleeve 70. The end surface of the number sleeve 70 is provided with a pattern of holes spaced around the annular end surface. The holes may be formed with a particular shape and size. The shape and/or size of the holes may identify the medicament. The edge of the annular end surface is provided with a plurality of teeth, arranged to extend from the end surface of the number sleeve in an radial direction of the device. The plurality of teeth may be formed with a particular shape or profile. The shape or profile of the teeth may identify the medicament.

Any combination of radial and/or axial teeth and/or holes formed in or on the annular end surface may be provided to increase the accuracy of detection.

The processor 50 calculates an amount of rotation of the number sleeve 70 during the dose dispensing operation. From the amount of rotation, the delivered dose can be calculated. This may be done by the data collection device 20 or by another computing device. In general, any component which is located close to the dose setting dial and which rotates when a dose is dispensed from the injection device 1 may be used as the internal component having the pattern of relatively reflective and non-reflective regions formed on a surface thereof.

The data collection device of the present disclosure attaches directly to the dose setting dial of the medicament administration device. Previous data collection devices have attached to the main housing of the medicament administration device. This can impede the use of the medicament administration device by a user. Many such devices attach over a dose indication window in the housing of the medicament administration device. This obscures the dose indication window, making the user wholly reliant on the data collection device to indicate the dialed dose, which may reduce user confidence in the medicament administration device. Such devices cannot determine the type of medicament dispense by the medicament administration device from the dose indication window alone. Some other such devices require an additional cut out or aperture in the housing of the medicament administration device in order to view or connect with an internal moveable component. Cutting out a part in the housing of the medicament administration device makes the ingress of dust and dirt inside the delivery mechanism more likely. It may also present problems relating to the sterility of the medicament administration device.

The data collection device of the present disclosure is able to identify the medicament dispensed from the medicament administration device remotely, and monitor the amount of the medicament which is dispensed, without contacting or being secured to the main housing of the medicament administration device. The data collection device is configured to attach to and to effectively replace the part of the medicament administration device with which the user would normally interact. When a user wishes to dial a dose, they grasp and rotate the housing 21 of the data collection device 20 which in turn rotates the dose setting dial 12. The user can continue to observe the mechanical dose indication window 13 of the medicament administration device. When the user wishes to inject a dose, they exert a force on the proximal end of the data collection device. This in turn communicates a force to the dose setting dial. Where the medicament administration device has a dose delivery button 11, the button 26 of the data collection device is configured to depress relative to the housing 21 and therefore to depress the dose delivery button 11 in turn. Therefore a user would notice no material difference in the way in which they operate the medicament administration device as a result of the addition of the data collection device according to the present disclosure.

The data collection device is able to record the number of dosages and the amount of medicament dispensed for more than on type of medicament administration device, and separately monitor each identified medicament.

The data collection device of the present disclosure may use an ultrasonic sound to identify the pattern. This allows the external components of the medicament administration device to be made out of a plastic or other material which is opaque to light, but transparent or transparent to ultrasound. No additional cut out, aperture or the like are required for the ultrasonic detector to detect the pattern provided on the number sleeve 70.

Alternatively, the data collection device may use light as an illumination source. The external components of the medicament administration device may be made out of a plastic or other material which is transparent or partially transparent to light. Only the appropriate areas of the medicament administration device may be made of the transparent material, effectively forming a window or, alternatively an opening or aperture may be formed.

In this embodiment, the pattern on the number sleeve 70 may be formed as a pattern of relatively reflective and non-reflective regions on the annular end surface. For example, reflective and non-reflective sections may be arranged alternately. During a dose dispensing operation, a light source illuminates the part of the number sleeve 70 including the pattern of relatively reflective and non-reflecting regions; and an optical sensor receives the light reflected by at least the relatively reflective regions. Relatively reflective and non-reflective regions may be, for example, different colours e.g. black and white.

Alternatively, the data collection device may use infrared light as an illumination source. This allows the external components of the medicament administration device to be made out of a plastic or other material which is opaque to optical wavelengths, but transparent or partially transparent to Infrared wavelengths. No additional cut out, aperture or the like are required, although only the appropriate areas of the medicament administration device may be made of the IR transmissive material, effectively forming an Infrared 'window'.

The relatively reflective and non-reflective regions of the pattern may be printed, deposited, etched or otherwise created directly onto the number sleeve 70 or other suitable internal component during that component's manufacture. The medicament administration device may then be assembled in the same way as before, using the same assembly method and tools. Therefore, only very minimal modification of the medicament administration device design and creation is required in order to implement the disclosure.

Figure 5:
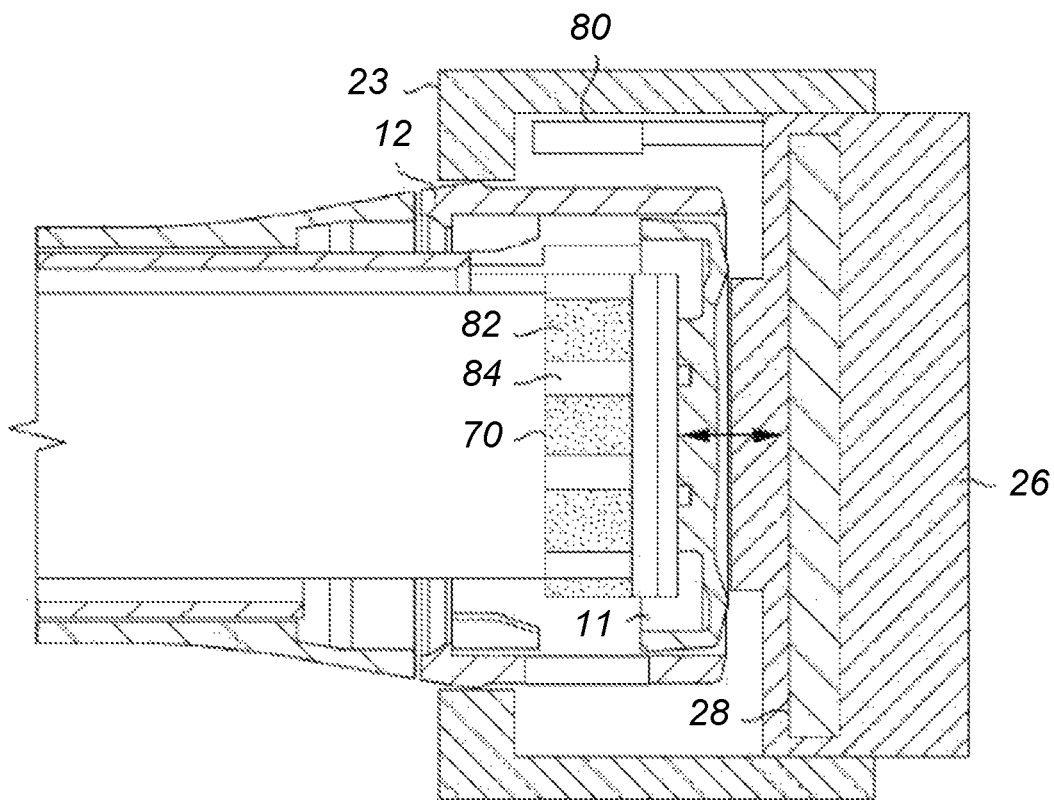
FIG. 5 illustrates a further alternative arrangement for the components of a data collection device.

Referring to FIG. 5, an alternative embodiment is shown. In some embodiments, instead of having an ultrasonic source or a light source and a detector/sensor, the electronics assembly may include a passive sensor only. In this embodiment, the electronics assembly comprises a non-contact magnetic sensor 80, for example a Hall sensor. In this embodiment, the rotatable component 70 comprises a series of magnetic regions 82 and non-magnetic regions 84 spaced alternately around the circumference of the rotatable component 70. The magnetic regions 82 may be permanent magnets, such as regions containing magnetic particles or a magnetic ink. As the magnetic and non-magnetic regions, 82, 84, rotate past the magnetic sensor 80 during dose dispense, the magnetic sensor 80 detects a pattern in the change in the strength and optionally direction of the magnetic field. This information can then be used to identify the medicament and to determine the amount (angle) of rotating of the rotatable component 70.

In this embodiment, the magnetic sensor 80 is supported in a recess between the dose setting dial 12 and an internal surface of the attachment assembly 23. For example, the magnetic sensor 80 may be supported on a protrusion of the electronics assembly 24. The attachment assembly 23 may have a recess to allow space for this protrusion. In this embodiment, the series of magnetic regions 82 and non-magnetic regions 84 are disposed on an outer surface of the number sleeve 70, around the circumference. Such an arrangement may allow the series of magnetic regions 82 and non-magnetic regions 84 to be larger or spaced further apart as more space is available on this surface of the number sleeve 70.

The dose setting dial 12 is transmissive or partially transmissive to the magnetic field generated by the magnetic regions 82, allowing the magnetic sensor 80 to detect rotation of the rotatable component 70 remotely and without the need for a cut-out or aperture in the dose setting dial 12. This embodiment may allow the distance between the magnetic sensor 80 and the series of magnetic regions 82 and non-magnetic regions 84 to be minimized and to remain unchanged when the dose delivery button 11 is depressed. This adds to increased dose detection reliability. This embodiment also has a simple mechanical design and construction. The attachment assembly 23 of this embodiment may have a wider diameter compared to that of FIG. 3 to allow room for the magnetic sensor 80. This may reduce the force needed by the user to rotate the dose setting dial 12 during dose dialling and therefore improve the ease of use for users with reduced dexterity.

Although FIG. 5 shows the magnetic sensor 80 arranged radially relative to the dose setting dial 12, the magnetic sensor 80 may instead by located proximally of the dose setting dial 12, in the same manner as shown in FIG. 3.

In an alternative embodiment, the electronics assembly comprises an acoustic detector, for example a microphone, and the rotatable component 70 comprises one or more piezo-electronic transducers spaced around the circumference of the rotatable component 70. The piezo-electronic transducers are each configured to emit sound with, for example, a certain intensity, tone or pitch. As the piezo-electronic transducers rotate past the microphone during dose dispense, the microphone can detect a change in the intensity, tone or pitch of the emitted sound. This information can then be used to identify the medicament and to determine the amount (angle) of rotating of the rotatable component 70. Alternatively, each piezo-electronic transducer may emit a time-varying sound signal, which can be detected by the microphone and identified by the processor arrangement 50.

Figure 6:
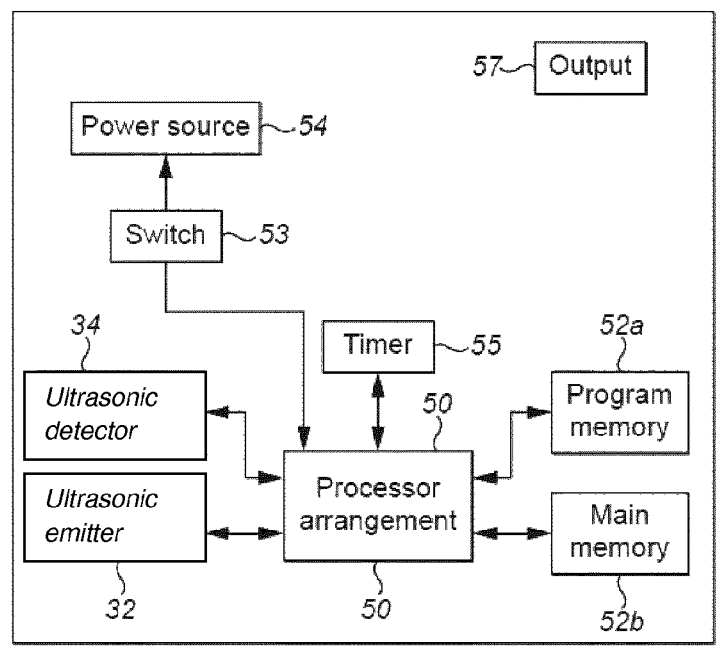
FIG. 6 is a block diagram of the data collection device.

FIG. 6 is a block diagram of the data collection device 20. The data collection device 20 includes a processor arrangement 50 including one or more processors, such as a microprocessor, a Digital Signal Processor (DSP), Application Specific Integrated Circuit (ASIC), Field Programmable Gate Array (FPGA) or the like, together with memory units 52a, 52b, including program memory 52a and main memory 52b, which can store software for execution by the processor arrangement 50. The data collection device includes the ultrasonic source 32 and the ultrasonic detector 34. The processor arrangement 50 controls operation of the ultrasonic source 32 and receives signals from the ultrasonic detector 34.

The data collection device 20 has a power source 54 which may be a battery, for example a coin cell. The data collection device 20 may optionally include a switch 53 configured to be triggered when or shortly before a dose is dispensed. To this end, the switch 53 may include a pressure or touch sensitive area in the end plate 22 or button 26 of the data collection device 20, for example a piezoelectric switch. The switch 53 may control application of power from the power source 54 to the processor arrangement 50 and other components of the data collection device 20. In embodiments in which the electronics assembly 24 and attachment assembly 23 are configured to move longitudinally relative to each other, the switch 53 may be implemented mechanically. For example, electrodes may be disposed on an internal surface of the attachment assembly 23 and corresponding electrodes on the electronics assembly 24 may make contact (and hence complete a circuit) when the button 26 is depressed. This may then trigger the wake-up of the other electronics, including the light source and optical sensor.

A timer 55 is also included. The processor arrangement 50 may use the timer 55 to monitor a length of time that has elapsed since an injection was completed, determined using the switch 53. Also optionally, the processor arrangement 50 may compare the elapsed time with a predetermined threshold, to determine whether a user may be attempting to administer another injection too soon after a previous injection and, if so, generate an alert such as an audible signal and/or generate an optical signal such as blinking one or more LEDs. The data collection device 20 may comprise a number of LEDs or other light sources for providing optical feedback to a user. For example, the LEDs may use different colours and/or lighting patterns such as blinking with constant or changing periodicity. On the other hand, if the elapsed time is very short, it may indicate that the user is administering a medicament amount as a "split dose", and the processor arrangement 50 may store information indicating that a dosage was delivered in that manner. In such a scenario the elapsed time is compared with a predetermined threshold in the range of a few seconds, e.g. 10 seconds up to a few minutes, e.g. 5 minutes. According to an example the predetermined threshold is set to 2 minutes. If the time elapsed since the last injection is two minutes or less, the processor arrangement 50 stores information indicating that the dosage was delivered as a "split dose". Another optional purpose for monitoring the elapsed time by the processor arrangement 50 is to determine when the elapsed time has passed a predetermined threshold, suggesting that the user might have forgotten to administer another injection and, if so, generate an alert.

The processor is further configured to store data relating to date and/or time information, data relating to information from the ultrasonic detector 34, or combinations thereof. In particular, the memory is configured to store a combination of date and/or time information, medicament identification information, and internal component rotation information retrieved from the ultrasonic detector 34 output data. In this way the memory is able to store a log that provides a history of information on number sleeve 70 (or other internal component) rotation. Data can for example be stored in the main memory 52b. Alternatively, data may be stored is a separate data storage section (not shown) of the memory.

Since the number sleeve or other internal component rotates as medicament is expelled from the injection device 1, the angle of rotation measured by the ultrasonic detector 34 is proportional to the amount of medicament expelled. It is not necessary to determine a zero level or an absolute amount of medicament contained in the injection device 1. In this way the sensor arrangement is less complex than compared to a sensor arrangement that is configured for absolute position detection. Moreover, since it is not necessary to monitor the numbers or tick marks on the number sleeve 70 displayed through the dosage window 13, the data collection device 20 may be designed so that it does not obscure the dosage window 13.

Figure 7:
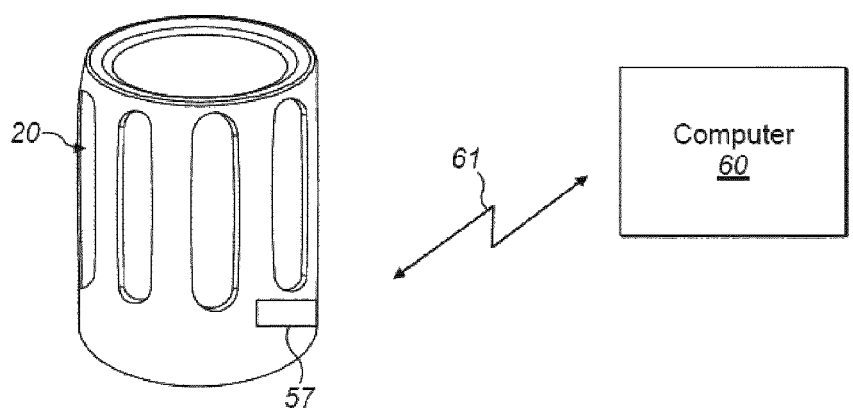
FIG. 7 shows a system in which the data collection device is connected to another device, such as a personal computer.

An output 57 is provided, which may be a wireless communications interface for communicating with another device via a wireless network such as wi-fi, Bluetooth®, or NFC, or an interface for a wired communications link, such as a socket for receiving a Universal Series Bus (USB), mini-USB or micro-USB connector. FIG. 7 depicts an example of a system in which the data collection device 20 is connected to another device, such as a personal computer 60, via a wireless connection 61 for data transfer. Alternatively or in addition, the data collection device 20 may be connected to another device via a wired connection. For example, the processor arrangement 50 may store determined number sleeve 70 rotation angles and time stamps (including date and/or time) for the injections as they are administered by the user and subsequently, transfer that stored data to the computer 60. The computer 60 may be configured to calculate an administered dose based on further information entered by the user or a medical professional regarding the type of injection device and the type of medicament. The computer 60 maintains a treatment log and/or forwards treatment history information to a remote location, for instance, for review by a medical professional.

According to some embodiments, the data collection device 20 may be configured to store data such as medicament identification, number sleeve 70 rotation angles and time stamps of up to 35 injection events. According to a once-daily injection therapy this would be sufficient to store a treatment history of about one month. Data storage is organized in a first-in first-out manner ensuring that most recent injection events are always present in the memory of the data collection device 20. Once transferred to a computer 60 the injection event history in the data collection device 20 will be deleted. Alternatively, the data remains in the data collection device 20 and the oldest data is deleted automatically once new data is stored. This way the log in the data collection device is built up over time during usage and will always comprise the most recent injection events. Alternatively, other configuration could comprise a storage capacity of 70 (twice daily), 100 (three months) or any other suitable number of injection events depending on the therapy requirements and/or the preferences of the user.

In another embodiment, the output 57 may be configured to transmit information using a wireless communications link and/or the processor arrangement 23 may be configured to transmit such information to the computer 60 periodically.

The specific embodiments described in detail above are intended merely as examples of how the present disclosure may be implemented. Many variations in the configuration of the data collection device 20 and/or the injection device 1 may be conceived.

In particular, while the embodiments above have been described in relation to collecting data from an insulin injector pen, it is noted that embodiments of the disclosure may be used for other purposes, such as monitoring of injections of other medicaments or a plurality of different medicaments.

The data collection device 20 may optionally include a display (not shown), which could for example occupy the end plate 22 of the data collection device 20. Various information can be displayed, such as the length of time that has elapsed since an injection was completed, and warning messages where a user is attempting to administer another injection too soon after a previous injection.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A data collection device comprising:
an attachment assembly for attaching the data collection device directly to a dose setting dial of a medicament administration device such that the attachment assembly can rotate with the dose setting dial;
a processor arrangement; and
a sensor configured to detect an identifier provided on a surface of an internal component of the medicament administration device,
wherein the sensor comprises an ultrasound sensor configured to detect the identifier,
wherein the internal component rotates during a medicament delivery, and
wherein the processor arrangement is configured to determine, from signals received from the sensor, an amount of rotation of the internal component.

2. The data collection device of claim 1, wherein the sensor is supported on a side of the data collection device which abuts the dose setting dial of the medicament administration device.

3. The data collection device of claim 1, wherein the attachment assembly is configured to releasably attach the data collection device to the dose setting dial of the medicament administration device such that the dose setting dial of the medicament administration device is disposed between the sensor and the surface of the internal component.

4. The data collection device of claim 1, wherein the processor arrangement is configured to receive signals from the sensor and to determine an identity of a medicament delivered from the medicament administration device based on the identifier that is detected.

5. The data collection device of claim 4, wherein the processor arrangement is further configured to detect an occurrence of a medicament delivery from the medicament administration device.

6. The data collection device of claim 5, wherein the processor arrangement is further configured to determine a time stamp for the occurrence of the medicament delivery and to store a determined medicament dosage and the time stamp.

7. The data collection device of claim 1, wherein the sensor comprises an optical sensor.

8. The data collection device of claim 1, wherein the medicament administration device comprises a medicament.

9. A system comprising:
a medicament administration device comprising:
a dose setting dial, and
an internal component that rotates around a longitudinal axis of the medicament administration device when a dose of medicament is delivered from the medicament administration device, the internal component comprising a surface and an identifier formed on the surface; and
a data collection device comprising:
an attachment assembly for attaching the data collection device directly to the dose setting dial, and
a sensor configured to detect the identifier,
wherein the sensor comprises an ultrasound sensor configured to detect the identifier.

10. The system of claim 9, wherein the sensor is supported on a side of the data collection device which abuts the dose setting dial of the medicament administration device.

11. The system of claim 9, wherein the attachment assembly is configured to releasably attach the data collection device to the dose setting dial of the medicament administration device such that the dose setting dial of the medicament administration device is disposed between the sensor and the surface of the internal component.

12. The system of claim 9, wherein the data collection device comprises a processor arrangement configured to receive signals from the sensor and to determine an identity of a medicament delivered from the medicament administration device based on the identifier that is detected.

13. The system of claim 12, wherein the processor arrangement is further configured to detect an occurrence of a medicament delivery from the medicament administration device.

14. The system of claim 13, wherein the processor arrangement is further configured to determine a time stamp for the occurrence of the medicament delivery and to store a determined medicament dosage and the time stamp.

15. The system of claim 12, wherein the identifier is provided on the surface of the internal component which rotates during a medicament delivery, and wherein the processor arrangement is further configured to determine, from the signals receives from the sensor, an amount of rotation of the internal component.

16. The system of claim 9, wherein the sensor comprises an optical sensor.

17. The system of claim 9, wherein the medicament administration device comprises a medicament.

18. A data collection device comprising:
an attachment assembly for attaching the data collection device to a dose setting dial of a medicament administration device; and
a sensor configured to detect an identifier provided on a surface of an internal component of the medicament administration device, wherein the sensor comprises an ultrasound sensor configured to detect the identifier formed on the surface of the internal component of the medicament administration device,
wherein a processor arrangement is configured to receive signals from the sensor and to determine a type of a medicament delivered from the medicament administration device based on the identifier that is detected.

19. A system comprising:
  a medicament administration device comprising:
    a dose setting dial, and
    an internal component comprising a surface and an identifier formed on the surface; and
  a data collection device comprising:
    an attachment assembly for attaching the data collection device to the dose setting dial,
    an ultrasound sensor configured to detect the identifier, and
    a processor arrangement configured to receive signals from the ultrasound sensor and to determine a type of a medicament delivered from the medicament administration device based on the identifier that is detected.

* * * * *